Figure 1:
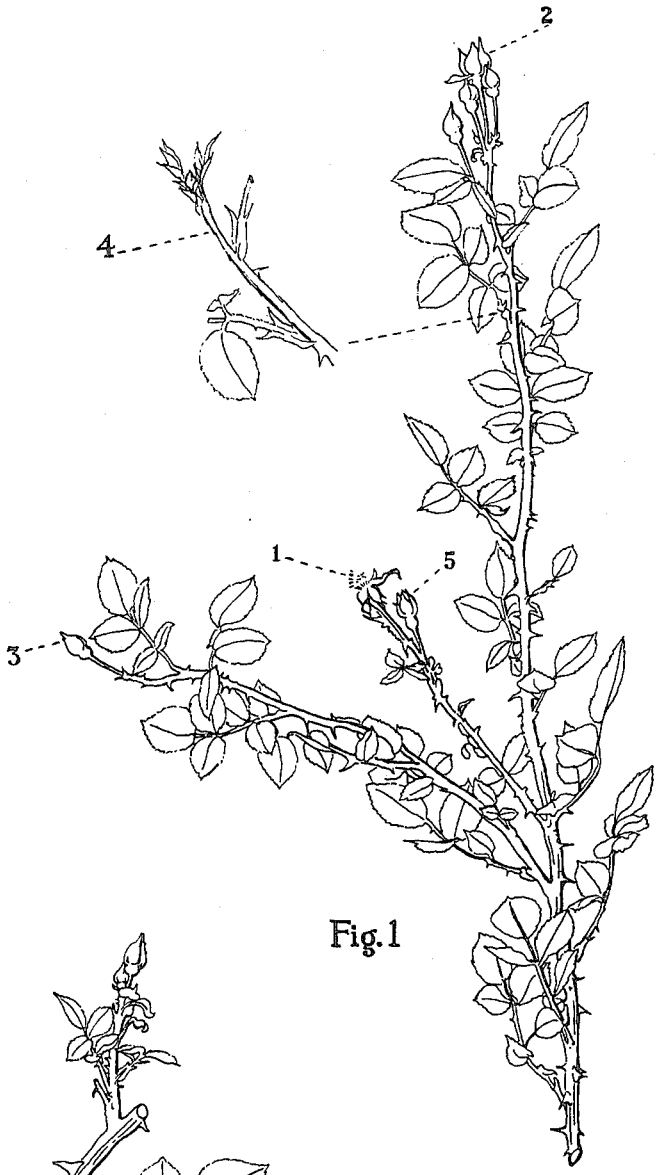
Figure 2:
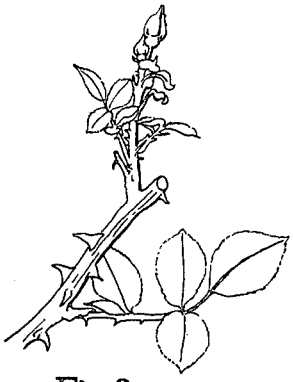

Aug. 18, 1931. H. F. BOSENBERG Plant Pat. 1

CLIMBING OR TRAILING ROSE

Filed Aug. 6, 1930

INVENTOR,
Henry F. Bosenberg.
Per
Agent.
Orville M. Kile

UNITED STATES PATENT OFFICE

HENRY F. BOSENBERG, OF NEW BRUNSWICK, NEW JERSEY, ASSIGNOR TO LOUIS C. SCHUBERT, OF NEW BRUNSWICK, NEW JERSEY

CLIMBING OR TRAILING ROSE

Application filed August 6, 1930. Serial No. 473,410.

My invention relates to improvements in roses of the type known as climbing or trailing roses in which the central or main stalks acquire considerable length and when given moderate support "climb" and branch out in various directions.

In roses it is very desirable to have a long period of blooming. This has been acquired in non-climbing roses of the type ordinarily called monthly roses or everblooming roses. My invention now gives the true everblooming character to climbing roses.

The following description and accompanying illustrations apply to my improvements upon the well known variety Dr. Van Fleet, with which my new plant is identical as respects color and form of flower, general climbing qualities, foliage and hardiness, but from which it differs radically in flowering habits —but the same everblooming habits may be attained by breeding this new quality into other varieties of climbing roses.

Figure I shows (1) a flower that is just dropping its petals, (2) a bud about to open, (3) a terminal bud just forming on a large side shoot, and (4) a new shoot which has not yet finished its growth and formed buds at its terminus. This shoot would not appear on the branch illustrated until several weeks later than the stage of development shown, when it would grow out ordinarily from the axil of the first or second leaf below the bloomed-off flower. (5) shows a second way in which new flowering shoots form, by branching off on a short stem immediately or closely adjacent to the blossom that has just finished blooming. Figure II shows a further method of branching and bud formation in cases where the bloom has been cut off, but the formation of new flowering shoots is not dependent upon pruning off the old blossoms. It is evident that this succession of blooms continuously or intermittently supplied by new shoots branching out throughout the summer and fall gives the true everblooming character. When grown in the latitude of New Brunswick, New Jersey, my new climbing rose named "The New Dawn" and illustrated herewith in exact drawings from photographs, provides a succession of blossoms on a single plant from about the end of May to the middle of November, or until stopped by frost.

No claim is made as to novelty in color or other physical characteristics of the individual blossoms, nor as to the foliage or growing habits of this rose other than as described above.

I claim:

A climbing rose as herein shown and described, characterized by its everblooming habit.

In testimony whereof I affix my signature hereunto.

HENRY F. BOSENBERG.